(12) United States Patent
Shaari

(10) Patent No.: US 7,888,049 B2
(45) Date of Patent: Feb. 15, 2011

(54) RAPID NASAL ASSAY KIT

(75) Inventor: Christopher M. Shaari, Demarest, NJ (US)

(73) Assignee: Toxcure. LLC, Hackensack, NJ (US)

( * ) Notice: Subject to any disclaimer, the term of this patent is extended or adjusted under 35 U.S.C. 154(b) by 318 days.

(21) Appl. No.: 11/672,440

(22) Filed: Feb. 7, 2007

(65) Prior Publication Data
US 2007/0184495 A1   Aug. 9, 2007

Related U.S. Application Data

(60) Provisional application No. 60/765,962, filed on Feb. 7, 2006.

(51) Int. Cl.
*G01N 33/53* (2006.01)
*G01N 31/00* (2006.01)

(52) U.S. Cl. ............ 435/7.21; 435/7.1; 436/1; 436/501; 436/518; 424/9.1; 424/520; 422/1; 422/50; 422/61; 530/300; 530/350

(58) Field of Classification Search ............ None
See application file for complete search history.

(56) References Cited

U.S. PATENT DOCUMENTS

| | | | |
|---|---|---|---|
| 4,703,017 A | 10/1987 | Campbell et al. | |
| 4,966,147 A | 10/1990 | Yaniv | |
| 5,910,421 A | 6/1999 | Small et al. | |
| 6,365,417 B1 | 4/2002 | Fleming et al. | |
| 6,551,791 B1 | 4/2003 | Small et al. | |
| RE38,430 E | 2/2004 | Rosenstein | |
| 6,764,849 B2 | 7/2004 | Small et al. | |
| 6,855,491 B2 | 2/2005 | Small et al. | |
| 6,998,273 B1 | 2/2006 | Fleming et al. | |
| 2002/0137117 A1 | 9/2002 | Small et al. | |
| 2005/0175992 A1* | 8/2005 | Aberl et al. ............ 435/5 |

OTHER PUBLICATIONS

Sobol et al. "Inflammatory Patterns of Allergic and Nonallergic Rhinitis," Current Allergy and Asthma Reports. vol. 1 (2001) 193-201.*
M. Dykewicz, et al. Diagnosis and Management of Rhinitis: Complete Guidelines of the Joint Task Force on Practice Parameters in Allergy, Asthma and Immunology, 81 Ann Allergy Asthma Immunol 478-518 (1998).
M. Niehaus, et al. Lactoferrin and Eosinophilic Cationic Protein in Nasal Secretions of Patents with Experimental Rhinovirus Colds, Natural Colds, and Presumed Acute Community-Acquired Bacterial Sinusitis 38 J. Clin. Microbio. 3100-3102 (Aug. 2000).
A. Elhini, et al., Th1 and Th2 Cell Population in Chronic Ethmoidal Rhinosinusitis: A Chemokine Receptor Assay, 115 Laryngoscope 1272-1277 (Jul. 2005).
P. Howarth, Leukotrienes in Rhinitis, 161 Am J Respir Crit Care Meds, S133-S136 (2000).
H. Riechelmann, et al., Biological Markers in Nasal Secretions, 21 Eur Respir J 600-605 (2003).

* cited by examiner

*Primary Examiner*—Lisa V Cook
(74) *Attorney, Agent, or Firm*—Frommer Lawrence & Haug LLP

(57) ABSTRACT

The present invention relates to an assay which can be used on nasal secretions. The assay is used to determine the cause of nasal secretions, for example whether the secretions are due to an allergic reaction or a non-allergic reaction.

16 Claims, 4 Drawing Sheets

THE TESTS

TEST #1: DIAGNOSIS
Do I need to see a doctor for my condition?

RESULT:
If Lactoferrin lights up, goto doctor.

Test #2: DIAGNOSIS AND TREATMENT
Do I need to see a doctor? If not, how do I treat myself?

RESULT:
If lactoferrin lights up, goto doctor.
If lactoferrin does NOT light up, look at IL-4 result:
If IL-4 is positive, try antihistamines and nasalcrom.
If IL-4 is negative, try mucolytics and saline spray,
   but    avoid antihistamines or nasalcrom.

TEST #3: PROFESSIONAL VERSION
For use in research, or having patient track levels of chemicals during an "attack"
(e.g. a 'nasal diary' may help differentiate nasal conditons, or differentiate migraine from nasal conditions)

Would include/involve:
Diagnostic tests for individual cytokines, chemokines, receptors, etc...

Endoscopic retrieval methods with filter papers, polyurethane foams or others.

FIG 2C

RAPID NASAL ASSAY KIT

This application claims priority from provisional application No. 60/765,962, filed Feb. 7, 2006, which is incorporated herein by reference in its entirety.

BACKGROUND

The present invention relates to a rapid nasal assay kit, which can determine the cause of nasal secretions. For a general review of rhinitis, its diagnoses and treatment, reference is made to M. Dykewicz, et al. Diagnoses and Management of Rhinitis: Complete Guidelines of the Joint Task Force on Practice Parameters in Allergy, Asthma and Immunology, 81 Ann Allergy Asthma Immunol 478-518 (1998), incorporated herein by reference in its entirety.

Definition

Rhinitis is defined as a disorder characterized by a one or more of the following nasal symptoms: nasal congestion, rhinorrhea, sneezing, itching of the nose and/or post nasal drainage.

Classification

Rhinitis is classified by etiology as allergic or non allergic. Allergic rhinitis can be seasonal, perennial, episodic or occupational. Non allergic rhinitis can be infectious, perennial (or vasomotor rhinitis), NARES (non allergic rhinitis with eosinophilia syndrome), reflex induced (such as chemical), occupational or caused by atrophy, hormones, exercise or medication induced.

Prevalence

Chronic rhinitis symptoms are among the most common problems presenting to a physician. It has been estimated that 20 percent of the U.S. population has allergic rhinitis, or approximately 58 million people. Population survey results have estimated that 19 million Americans suffer from non allergic rhinitis.

Allergic Rhinitis

The symptoms of allergic rhinitis are often mediated by an IgE-mast cell-Th2 lymphocyte immune response. Allergic or atopic individuals respond to specific antigens according to the following mechanism: the antigen is processed by an antigen presenting cell (APC) and delivered to CD4+lymphocytes that release interleukin (IL)3, IL4, IL-5, and granulocyte macrophage colony stimulating factor (GMCSF) and other cytokines. These promote IgE production against these allergens by plasma cells, mast cell proliferation and infiltration of airway mucosa and eosinophilia.

An early phase for immediate allergic response may occur. IgE coated mast cells move into the epithelium, recognize mucosally-deposited allergen, and degranulate. Mast cell products include preformed mediators such as histamine, tryptase (a mast cell specific marker), chymase, kininogenase, heparin and other enzymes. ProstaglandinD2, and the cysteinyl-leukotrienes LTC4, LTD4 and LTE4 are also released. These mediators stimulate the vessels to leak and produce edema plus watery rhinorrhea, and dilate arteriole venule anastomoses causing nasal congestion. Release of these mast cell mediators and induction of these reactions occur within minutes and are termed the immediate or early allergic response.

A latent phase response is characterized primarily of nasal congestion. The mast cell mediators, including the cytokines, are thought to act upon post capillary endothelial cells to promote VCAM and E-selectin expression that permits lymphocytes to stick to the endothelial cells. Chemoattractants, such as IL-5 for eosinophils, promote the infiltration of the superficial lamina propria of the mucosa with some neutrophils and basophils, many eosinophils, and at a later time, T-lymphocytes and macrophages. Over the course of 4 to 8 hours these cells become activated and release their mediators, which activate many proinflammatory reactions of the immediate phase. Eosinophil products such as major basic protein, eosinophil cation protein, hypochlorate, leukotrienes and others are thought to damage the epithelium and other cells, inflammatory response that promotes the tissue damage of chronic allergic conditions.

TH2 lymphocytes are thought to play a critical role in promoting the allergic response by releasing their combination of IL-3, IL-4 and IL-5 and other cytokines that promotes IGE production, eosinophil chemoattraction and survival in tissues, and mast cell recruitment. The cytokines released from the TH2 lymphocytes, mast cells, eosinophils, basopbils and epithelial cells may circulate and cause fatigue, malaise, irritability and neurocognitive deficits that commonly affect those suffering from allergic rhinitis.

Non Allergic Rhinitis

When allergic causes of rhinitis have been excluded as the cause of rhinitis, a number of nasal conditions of partly unknown etiology and pathophysiology remains. This category is known as non allergic rhinitis and includes infectious rhinitis, hormonal rhinitis, vasomotor rhinitis, non allergic rhinitis with eosinophilia syndrome (NARES), certain types of occupational rhinitis and gustatory and drug induced rhinitis.

NARES is characterized by nasal congestion and prominent nasal eosinophilia. Neutrophilia infiltrates are usually seen with infectious rhinitis. LTB4, IL-7, bacterial products and complement fragments may activate neutrophils. The neutrophils may be seen in viral rhinitis syndromes as well. In addition, an increase in TH1 lymphocytes is indicative of non-allergic rhinitis. Other forms of non allergic rhinitis can be accounted for by hormonal changes, drug induced or idiopathic causes.

Diagnosis

Technically the diagnosis of allergic rhinitis is made by history, physical exam and specific IgE testing. The history focuses on allergic triggers, history of other associated allergic symptoms, past treatment experience and family history of allergies. The typical physical examination of the nasal mucosa reveals a pale and swollen mucosa with a blue gray appearance. Nasal secretions are typically watery and nasal congestion is common.

The demonstration of specific IgE antibodies to known allergens by skin testing or in vitro tests is important in determining whether the patient has allergic rhinitis. The other tests that help diagnose allergic rhinitis include anterior rhinoscopy, nasal endoscopy and imaging techniques such as a CAT scan, MRI or plain film radiographs to rule out associated sinusitis. Occasionally acoustic rhinomanometry is used to aerodynamically measure airway resistance. Nasal provocation tests using an allergen to determine whether an allergic reaction is produced, is unusual. Sometimes provocation testing with histamine or methacholine can be used to differentiate allergic from non allergic rhinitis, but there is frequent overlap between these conditions. Nasal cytology may aid in differentiating allergic rhinitis and NARES from other forms of non allergic rhinitis. Unproven forms of testing include cytotoxic testing, provocative and neutralization testing and measurement of specific and nonspecific IgG4.

Importance of Differentiating Allergic from Non Allergic Rhinitis

The first essential step in the treatment of rhinitis is to properly classify whether the patient has allergic or nonallergic rhinitis, since there is a fundamental difference in therapy. Allergic rhinitics are best treated with systemic antihistamines and mast cell stabilizers, and should avoid hyperosmolar saline sprays which can aggravate allergic symptoms. Conversely, nonallergic rhinitics should begin therapy with systemic decongestants, mucolytics and topical saline nasal sprays, and should strictly avoid antihistamines and mast cell stabilizers. The incorrect treatment of either condition leads to prolonged local and systemic symptoms and may even resulting complications such as acute or chronic sinusitis. With recent conversion of most antihistamines and decongestants to over-the-counter status, there is an increasing chance that the public will unknowingly take the wrong medicines. Similarly, if the public could rapidly diagnose the proper form of rhinitis, they can promptly and properly institute treatment, which would lead to significant cost savings by taking less medication, having fewer doctor visits and avoiding the progression to other complicated conditions such chronic sinusitis. Similarly, the health care professional treating a patient with a chronic or recurrent sinus or nasal condition is also often perplexed as to the exact etiology of the condition and treats the patient empirically, to see "how the patient responds" to a given form of therapy. If the patient does not respond favorably to a given therapy, other forms of therapy are given until the patient improves or requires referral to a specialist. This imposes and added burden on the patient with regard to time, cost and quality of life. The invention is also applicable to health care professionals that treat patients with sinus or nasal symptoms of disease.

Sinusitis is often a complication of chronic rhinitis and affects approximately 16 percent of the U.S. population, or about 32 million people. Chronic sinusitis accounts for about 11.7 million doctor visits annually. In 1996, overall health care expenditures attributable to chronic sinusitis in the U.S. were estimated to be over $5.8 billion. People suffering from chronic sinusitis miss an average of 4 days of work each year. A significant percent of chronic sinusitis results from nasal allergies that produce nasal edema and occlusion of the ostia of the sinuses. The treatment of sinusitis requires short-term and sometimes long-term antibiotic use as well as topical or oral steroid preparations and others.

Treatment

In general, most patients with allergic or non allergic rhinitis can be treated by over the counter medications, thanks in large part to the recent change in status of several popular prescription antihistamines and mucolytic/decongestants. The treatment of allergic rhinitis requires an oral antihistamine which blocks the action of histamine, and sometimes a mast cell stabilizer. Several non drowsy antihistamines are now available over the counter and include Claritin® and Allergra®. The mast cell stabilizer, cromolyn sodium, has been available over the counter for years. The treatment of non allergic rhinitis is with a mucolytic/decongestant often with saline nasal spray. In non allergic rhinitis, antihistamines are to be strictly avoided, especially with infectious rhinitis, as they may immediately worsen the symptom complex and rapidly lead to acute sinusitis. Topical nasal steroids which are still available by prescription only are useful in the treatment of both types of rhinitis.

What is needed is a rapid method of accurately determining which form or forms of rhinitis are present to help guide the patient to rapid, successful therapy.

SUMMARY OF THE INVENTION

It is an object of this invention to provide a rapid assay method and kit that differentiates allergic from non allergic rhinitis based on nasal secretions. This kit would be available over the counter or it can be used in healthcare provider offices. Secretions from the nose are sampled and assayed for chemicals or cells that are present in the various forms of rhinitis. Secretions can be collected by nose blowing, or by self-lavage and collected. Alternatively, physical (e.g. cold-air) or chemical stimuli (e.g. saline, hyperosmolar saline, methacholine, histamine) can be used to elicit secretions as well. Likewise, the present invention can be used to determine whether rhinitis is caused by an infection, the common cold, chronic sinusitis or other conditions.

BRIEF DESCRIPTION OF THE DRAWINGS

FIG. 2C shows a flow chart of tests of the present invention.

DETAILED DESCRIPTION OF THE INVENTION

Figure 1:
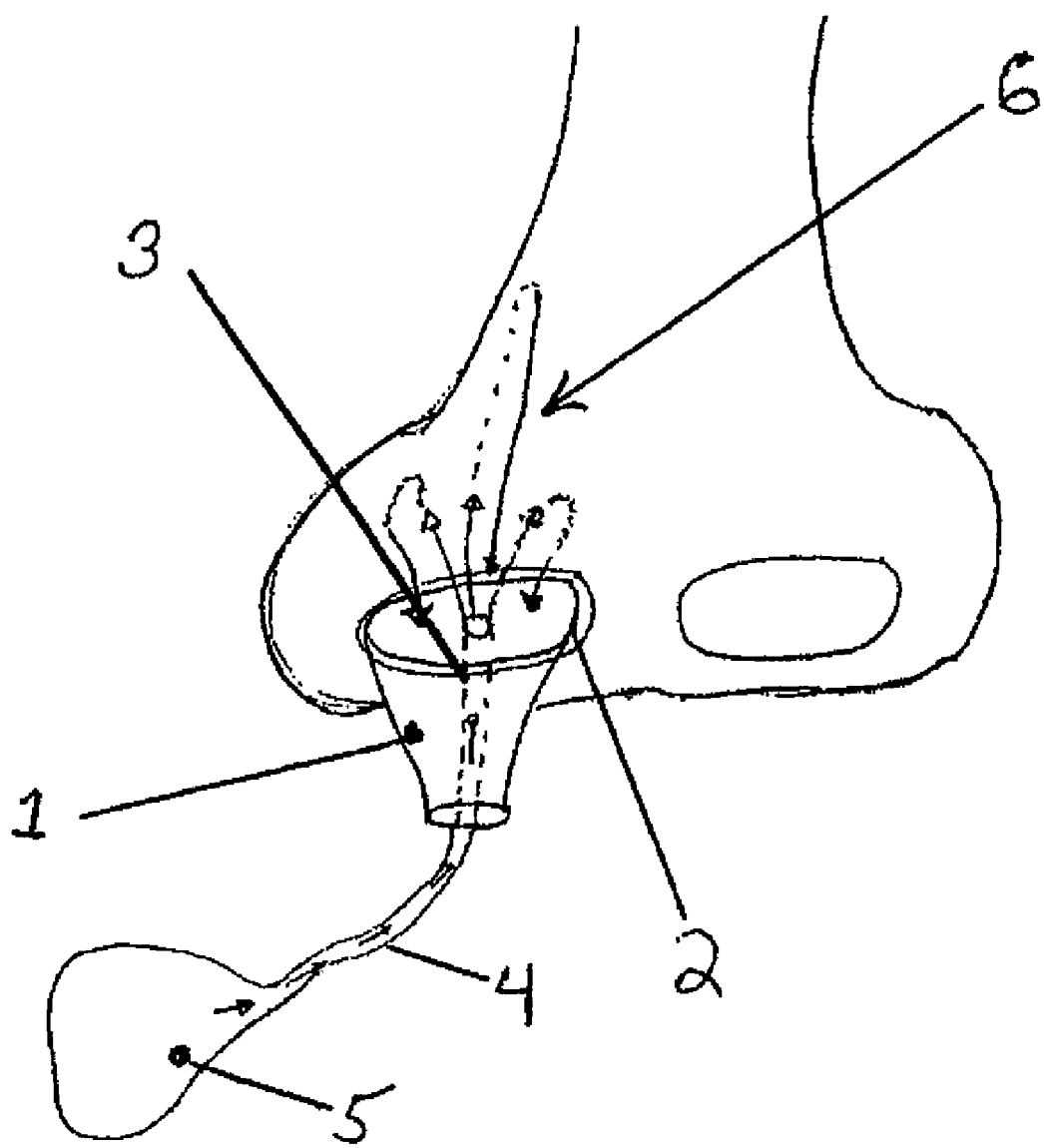
FIG. 1 shows one embodiment of the nasal secretion gathering means of the present invention.

Different types of rhinitis can be determined based on the cellular and/or chemical contents of the nasal secretion. The following is a partial list:

| Type Of Rhinitis with Cellular And Chemical Contents (non-inclusive) | | |
|---|---|---|
| TYPE | CELLS | CYTOKINES |
| INFECTIOUS | Neutrophils | IL8, IL1, IL6 |
|  | T-Lymphocytes (TH1) |  |
| COMMON COLD |  | INF-Gamma |
| Chronic Sinusitis |  | IL-1B, IL8, TNF-a |
| NONALLERGIC | Eosinophils | INF-Gamma |
|  | T-lymphocytes (TH1) | IL5, IL3, GM-CSF |
| ALLERGIC | Eosinophils | IL4, IL5, IL13 |
|  | T-lymphocytes (TH2) | GM-CSF, IL1-B |
|  |  | IL3 |

Other chemical mediators include Eosinophil Cation Protein, Histamine, LTC4, LTD4, LTE4, elastase.

The kit could assay using ELISA techniques for the presence of INF-G which is not present in allergic rhinitis. IF INF-G were present, the condition could not be allergic rhinitis and antihistamines should be avoided as part of the therapy. Instead, saline nasal sprays and systemic decongestants and mucolytic should be used. Alternatively the kit could analyze for the presence of IL4 or IL13 which are present in only allergic rhinitis. If IL4 or IL13 them were present, the patient should begin treatment with antihistamines and mast cell stabilizers, and avoid saline nasal sprays.

An alternative application of the kit is for patients with asthma to sample pulmonary secretions.

Alternatively, the kit could assay for the presence of TH2 cells or their mediators which appear to be a common cell type in allergic rhinitis. If the TH2 products are strongly present, the condition is likely to be allergic in origin. The kit could also assay for the presence of TH1 cells or mediators, which are conspicuously absent in allergic rhinitis. If the secretion is positive for TH1 cells or mediators, the condition is NOT allergic rhinitis.

There are a number of reagents, which can be used to test for TH1 or TH2 for the present invention. For example, TH1 cell specific antigen and TH2 cell specific antigen reagents are known. In addition, other reagents, which measure TH1, TH2 or the ratio of TH1 to TH2 are also envisioned for use with the present invention.

Exotaxin is another mediator found in patients with allergic rhinitis. Identification of this substance in nasal secretion would indicate allergic rhinitis as a cause of disease.

Reagents to measure the cells and cytokines identified in the above chart are known in the art For example, TH1 lymphocytes are known to preferentially express CCR5 and CXCR3. TH2 lymphocytes express CCR4, CCR8 and, to a lesser extent, CCR3. Antibodies against these compounds, for example, polyclonal antihuman CCR4 and polyclonal antihuman CCR5, are known. See A. Elhini, et al., Th1 and Th2 Cell Population in Chronic Ethmoidal Rhinosinusitis: A Chemokine Receptor Assay, 115 Laryngoscope 1272-1277 (July 2005), which is incorporated herein by reference in its entirety. Secondary antibodies, preferably labeled, such as biotinated antibodies, are also known. Id. So, far example, in a nasal secretion tested for the presence of CCR4, using polyclonal antibody CCR4 and a labeled secondary antibody, in for example, a sandwich assay, a positive reaction indicates the presence of CCR4, which shows the presence of TH2 lymphocytes, which indicates allergic rhinitis as opposed to non-allergic rhinitis. Other tests, such as the alkaline phosphatase antialkaline phosphatase (APAAP) test, using an alkaline phosphase antialkaline phosphatase kit and antihuman EG2 antibody can be used. Id. A positive reaction showing the presence of EG2 indicates the presence of TH2 lymphocytes. Thus, as with the above CCR4 test, a positive reaction shows that the rhinitis is allergic rhinitis, not non-allergic rhinitis. Other tests, such as testing for an RNA expressing either CCR4 or CCR5, can also be used.

Histamines, leukocytes and immunoglobulins (such as IgE) can also be tested, and their presence indicates allergic rhinitis. P. Howarth, Leukotrienes in Rhinitis, 161 Am. J. Respir. Crit. Care Med. S 133-S 136 (2000), incorporated herein by reference in its entirety.

Also, nasal secretions can be tested for eosinophilic cationic protein (ECP), the presence of which indicates that a patient has sinusitis or a cold. If the nasal secretions are then tested for nasal lactoferrin, the presence of lactoferrin indicates sinusitis and its absence indicates a cold. See M. Niehans, et al, Lactoferrin and Eosinophilic Catonic Protein in Nasal Secretions of Patients with Experimental Rhinovirus Colds, Natural Colds, and Presumed Acute Community-Acquired Bacterial Sinusitis, 38 J. Clin. Microbiol. 3100-31002 (August 2000), incorporated herein by reference in its entirety.

In the above-described procedures, the antibody (polyclonal or monoclonal) that reacts with the cell or cytokine to be determined is frequently called the capture antibody. The antibody that reacts with the cell or cytokine and capture antibody complex is frequently called the detection antibody. The detection antibody is labeled with, for example, biotin. In one aspect of the claimed invention, a standard sandwich assay is performed. The capture antibody can be bound to a solid surface, such as the bottom and/or sides of a well or a solid support. The nasal secretion is then contacted with the bound capture antibody. The nasal secretion can be applied directly, for example contacting the nasal secretion gathering means with the bound capture antibody, or the bound capture antibody can be placed in a solution or suspension and the nasal secretion gathering means is contacted with the solution or suspension.

After a sufficient time to allow the capture antibody to react with the nasal secretion, the detection antibody is added. The detection antibody can be labeled or the label can be added later. After the detection antibody has been given enough time to react, the test area, i.e., the well, solid support or other suitable container, is then examined. A positive reaction, usually indicated by a color change, indicates the presence of the tested for substance. In a preferred embodiment, the nasal secretion gathering means is removed prior to the addition of the detection antibody. Also, if appropriate, washing can occur prior to the addition of the detection antibody.

In the alternative embodiment, the capture antibody is attached to the nasal secretion gathering means. Then, after gathering the nasal secretion, the nasal secretion gathering means is contacted with the detection antibody, which can be labeled or the label can be added later. In one embodiment, the nasal secretion gathering means is contacted directly with the detection antibody. In another embodiment, the detection antibody is placed in solution or suspension and the nasal secretion gathering means is contacted with the solution or suspension. Also, depending on the amount of nasal secretions obtained, the nasal secretion gathering means can be washed prior to contacting it with the detection antibody.

The above list of chemical mediators is not meant to be limiting on the scope of the present invention. Any chemical unique to or predominantly found in allergic or non-allergic conditions can be employed. For example, the presence of neutrophils and IL6 are unique to infectious rhinitis. Polyclonal or momoclonal antibodies can be raised against neutrophils or IL6 and used as the capture antibody. A detection antibody can also be raised, again by conventional means. Using the above procedures, a test for infectious rhinitis can be generated. In the same respect, a test can be created for the common cold by testing for INF-Gamma, or chronic sinusitis by testing for ING-Gamma. The same concepts apply to the other mediators listed above.

In addition, the above discussion only discusses the use of one capture antibody and one detection antibody. More than one of each can be used. Preferably, each detection antibody will produce a different color. For example, a test can be configured that uses polyclonal antihuman CCR4 and ploycloral antihuman CCR5 with their respective detection antibodies. One detection antibody, for example the one for CCR4, will have a blue color and the other, for CCR5, will have a red color. In performing the above test, blue would indicate allergic rhinitis and red would indicate non-allergic rhinitis.

The amount of substance, reagent or reagents to use in the test depends upon the type of substance or reagent being used, what is being tested for and its concentration, and the size of the sample being tested. Generally, sufficient substance, or reagent or reagents is/are used so that a positive result can be determined and distinguished from a negative result. Determining the amount of substance, reagent or reagents to use is within the skill of the ordinary artisan.

In addition to the above kits, an alternative embodiment is shown in FIG. 1. This alternative device can be used to both irrigate the nose and collect nasal secretions. The device basically comprises a sponge (1) that fits in a nasal vestibule (nostril) (2). An atomizing/aerosoling device (3) is present, preferably in the center of the sponge (1). The atomizing/aerosoling device (3) is connected by a tube (4) to a container (5) which can, for example, contain sterile saline. Preferably, the container (5) contains 2-3 cc saline. Also, the container (5) is preferably squeezable.

In use, the sponge (1) is placed in one nostril (2) at a time. Then, the container (5) is activated, for example by squeezing it, which dispenses the saline solution into the nose and sinuses (6). The saline solution irrigates the nose and sinuses and then drops out towards the nostril. The sponge (1) absorbs at least some of this solution, which can them be analyzed by a procedure similar to the ones described above.

Although the above embodiment uses a sponge, any nasal secretion gathering means can be used. In one embodiment, the nasal secretion gathering means is an absorbent material, such as a cotton, including a cotton swab, gauze or a tissue. Also, while the above embodiment employs a nasal lavage, the nasal lavage need not be used.

In an alternative embodiment, lateral flow diagnostic technology can be employed. This technology is discussed in U.S. Pat. Nos. 6,365,417 and 6,998,273, which are incorporated herein by reference in their entirety. Here, a device for collecting nasal secretions includes a lateral flow chromatography strip having a collection pad for insertion into the nasal passage. The collection pad is separated from the remainder of the chromatography strip by a liquid impermeable removable barrier which prevents the nasal secretion in the collection pad from entering the chromatography strip. Once adequate nasal secretions have been collected (as indicated, for example, by a sample sufficiency indicator), the device is withdrawn from the nasal passage and the barrier is removed to allow the nasal secretions to flow through the strip. The nasal secretions interact with binding partners, for example capture antibodies and detection antibodies, on the strip to provide test results, for example the presence of CCR4. The strip may be contained in a housing with an access opening through which the removable barrier may be manipulated, and windows through which test results may be received.

Figure 2A:
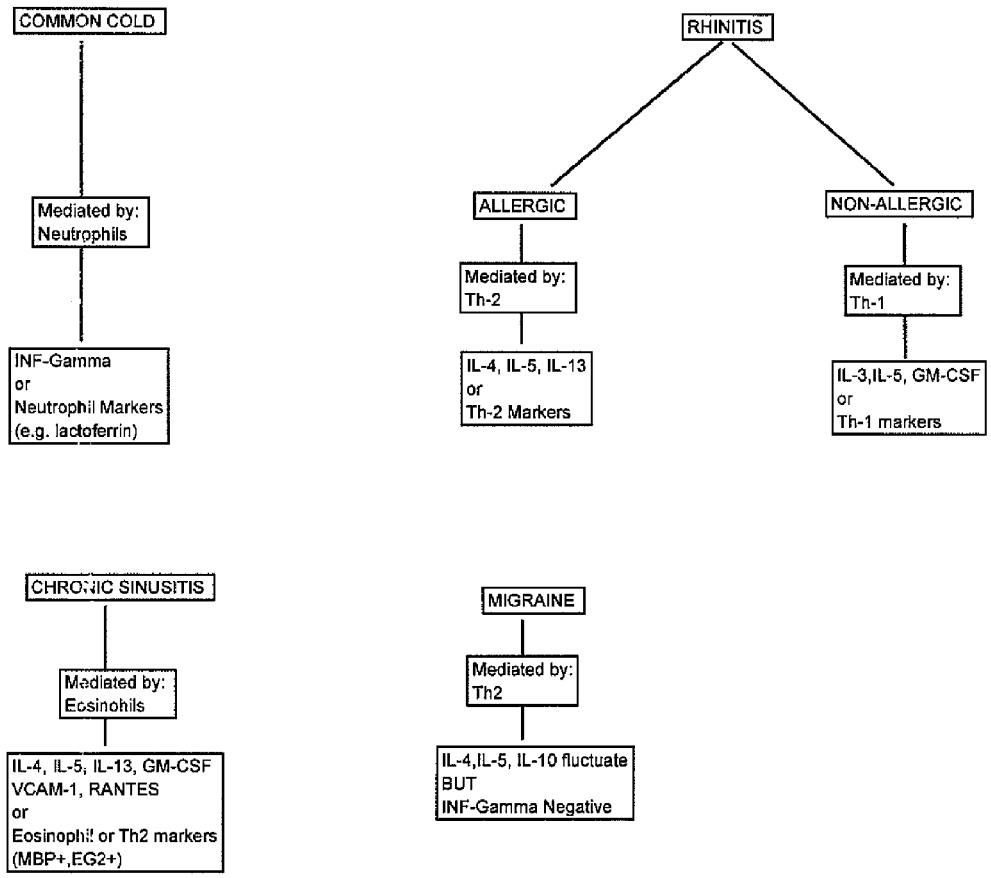
FIG. 2A shows a flow chart of a theory of the present invention.

FIG. 2 shows a flow chart or algorithm of the present invention. FIG. 2A shows the theory behind the invention, showing the cells and or chemicals found in the common cold, rhinitis, chronic sinusitis or migraine. FIG. 2A also identifies what can be assayed for and how one can retrieve a specimen for analysis.

Figure 2B:
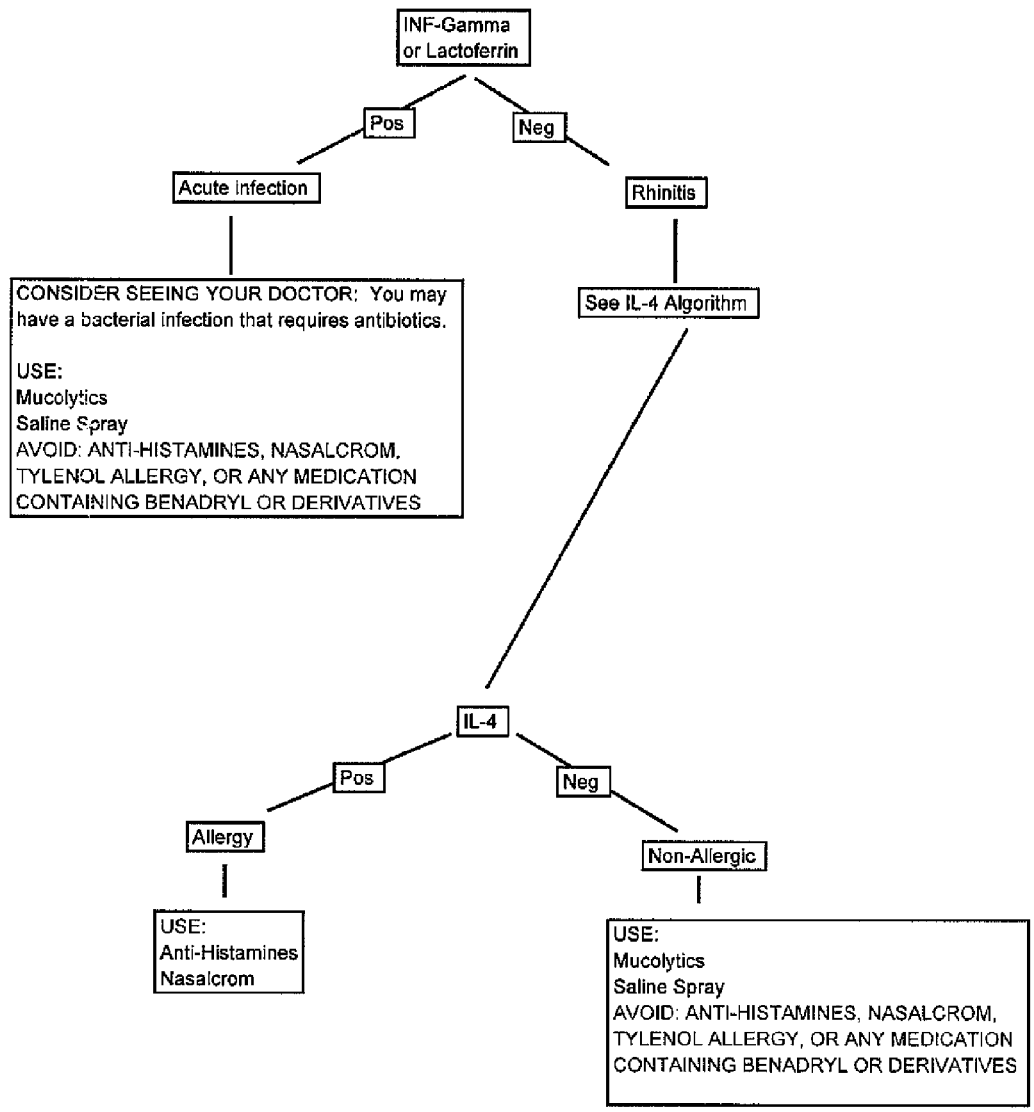
FIG. 2B shows a flow chart of assays of the present invention.

FIG. 2B shows sample assays to use. The first is for INF-Gamma or lactoferrin. A positive reaction shows an acute infection. The assay can also be configured so that if this first assay is positive, it is suggested to the patient that he or she see a doctor. Also, treatments and what to avoid can be suggested, as shown.

If the first assay is negative, then rhinitis is the diagnosis, and the direction is made to perform an IL-4 assay. If the IL-4 assay is positive, it is a diagnosis of allergic rhinitis. As above, the assay can be configured to advise the patient, e.g., what medications to take for treatment, as shown. If the IL-4 assay is negative, then the diagnosis is non-allergic rhinitis. The assay can also be configured to advise the patient which medications to take and avoid, as shown.

FIG. 2C shows some suggested tests. The first test, Test #1 is for diagnosis and shows a strip with a control and a lactoferrin test. As above in FIG. 2B, a positive means an acute infection and the patient should see a doctor.

The second test, Test #2, is for diagnosis and treatment. It shows a strip with a control, a lactoferrin assay and an IL-4 assay. As above, if the lactoferrin assay is positive the patient has an acute infection and should see a doctor. If the lactoferrin assay is negative and the IL-4 assay is positive, the diagnosis is allergic rhinitis and therapies can be suggested. If the lactoferrin assay and the IL-4 assay are both negative, then the diagnosis is non-allergic rhinitis and again, therapies can be suggested.

Also, envisioned is a Test #3, a professional version. As shown in FIG. 2C it can be used in research or to have a patient track levels of chemicals during an attack (e.g., a "nasal diary" may help differentiate nasal conditions or differentiate migraines form nasal conditions). Test #3 could also test for more cells, cytokines, etc. as detailed in FIG. 2A and throughout the specification.

Although the present invention has been described in relation to particular preferred embodiments and examples thereof, many variations and modifications and other uses may be made without departing from the invention. Accordingly, it is intended that all such alterations and modifications be included within the spirit and scope of the invention as disclosed herein. Further, all examples provided herein do not limit the scope of the invention.

What is claimed is:

1. A nasal secretion assay kit for the detection of non-allergic rhinitis comprising:
   a. a nasal secretion gathering means;
   b. a first capture antibody, which will react with and form a complex with a capture substance selected from the group consisting of TH1 cells, INF-Gamma, CCR5 and CXCR3;
   c. a first detection antibody, which will react with the complex in (a) and will generate a detectable response if the complex is present;
   d. a second capture antibody, which will react with and form a complex with IL-4; and
   e. a second detection antibody, which will react with the complex in (d) and will generate a detectable response if the complex is present,
      wherein the first detectable response is distinguishable from the second detectable response, and wherein the presence of a detectable response in (c) and the absence of a detectable response in (e) indicates that a nasal secretion is the result of a non-allergic rhinitis.

2. The nasal secretion assay kit of claim 1, wherein the response in (c) and/or (e) is detected using a sandwich ELISA.

3. The rapid nasal assay kit of claim 1, wherein the nasal secretion gathering means comprises:
   a. an absorbent material which fits into a nasal vestibule; and
   b. an atomizing or aerosoling device comprising a container and a tube, wherein the tube passes through the absorbent material such that when the container is contracted, its contents pass through the tube and irrigates the nose and sinuses, and the contents are then absorbed onto the absorbent material.

4. The rapid nasal assay kit of claim 1, wherein the nasal secretion gathering means is paper, tissue, or cloth.

5. The rapid nasal assay kit of claim 1, wherein the nasal secretion gathering means comprises:
   a. a sponge, which can fit into a nostril;
   b. an atomizing/aerosoling device, which passes through the sponge with a first end in communication with a sinus cavity, which is above the sponge; and
   c. a container attached to a second end of the atomizing/aerosoling device, wherein said container can contain a liquid.

6. The rapid nasal assay kit of claim 1, wherein the capture antibody in (b) and/or (d) is contained on the nasal secretion gathering means.

7. The rapid nasal assay kit of claim 1, wherein the detection antibody in (c) and/or (e) is contained on the nasal secretion gathering means.

8. The rapid nasal assay kit of claim 6, wherein the detection antibody in (c) and/or (e) is contained on the nasal secretion gathering means.

9. The rapid nasal assay kit of claim 1, wherein the detection antibody in (c), which has reacted with the complex in (b), generates a detectable response because the detection antibody is labeled.

10. The rapid nasal assay kit of claim 9, wherein the detection antibody is labeled prior to the reaction of the detection antibody with the complex.

11. The rapid nasal assay kit of claim 9, wherein the detection antibody is labeled after the detection antibody reacts with the complex.

12. The nasal secretion assay kit of claim 1, wherein the type of non-allergic rhinitis is selected from the group consisting of: hormonal rhinitis, vasomotor rhinitis, non allergic rhinitis with eosinophilia syndrome (NARES), occupational rhinitis, and gustatory and drug induced rhinitis.

13. The nasal secretion assay kit of claim 1, wherein the capture substance is INF-Gamma.

14. The rapid nasal assay kit of claim 1, wherein the detection antibody in (e), which has reacted with the complex in (d), generates a detectable response because the detection antibody is labeled.

15. The rapid nasal assay kit of claim 14, wherein the detection antibody is labeled prior to the reaction of the detection antibody with the complex.

16. The rapid nasal assay kit of claim 14, wherein the detection antibody is labeled after the detection antibody reacts with the complex.

* * * * *